Figure 1:
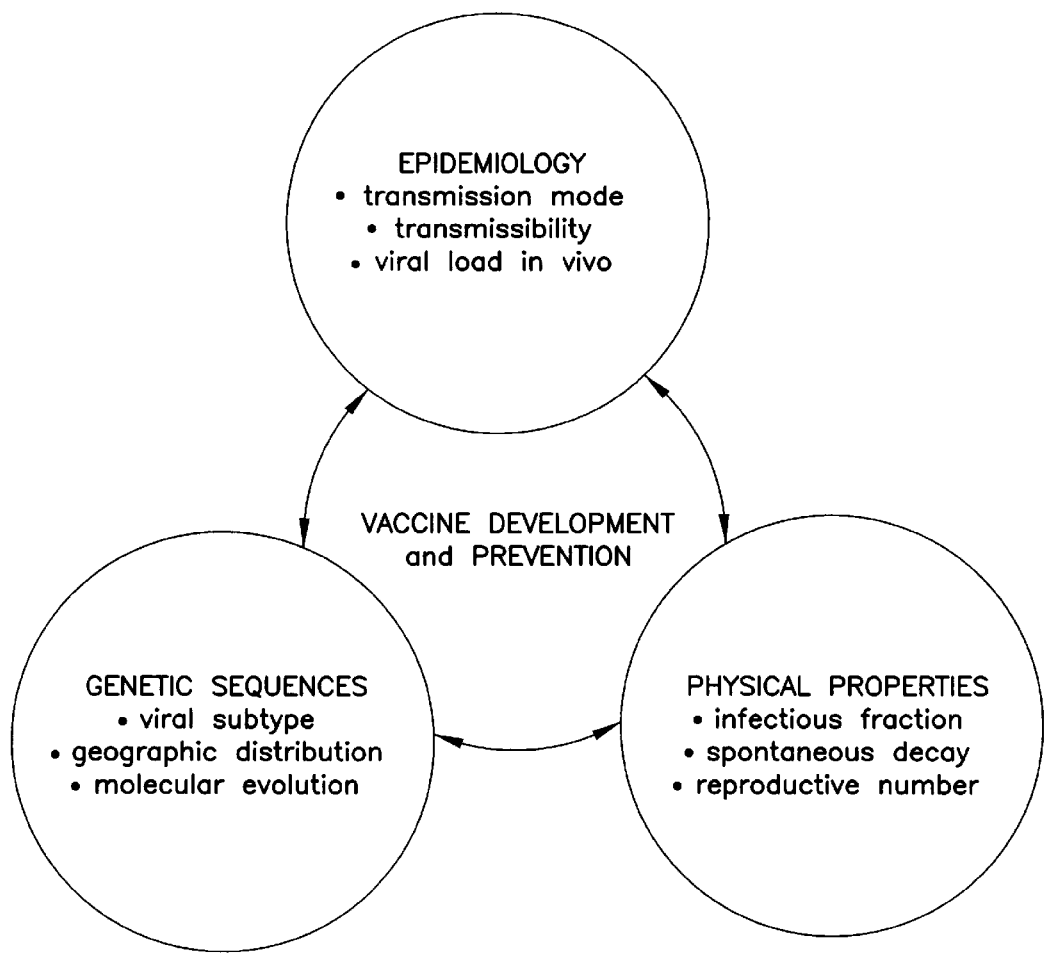

United States Patent [19]
Layne et al.

[11] Patent Number: 5,841,975
[45] Date of Patent: Nov. 24, 1998

[54] METHOD AND APPARATUS FOR GLOBALLY-ACCESSIBLE AUTOMATED TESTING

[75] Inventors: Scott P. Layne, Los Angeles, Calif.; Tony J. Beugelsdijk, Los Alamos, N. Mex.

[73] Assignee: The Regents of the University of California, Oakland, Calif.

[21] Appl. No.: 764,719

[22] Filed: Dec. 10, 1996

[51] Int. Cl.⁶ .................................................... H04N 1/413
[52] U.S. Cl. .............................. 395/200.33; 395/200.47; 345/329
[58] Field of Search ....................... 395/200.33, 200.47, 395/200.49, 200.57, 82, 84, 92; 345/329, 335, 336, 337; 348/12, 13

[56] References Cited

U.S. PATENT DOCUMENTS

| | | | |
|---|---|---|---|
| 4,231,087 | 10/1980 | Hunsberger et al. | 395/183.01 |
| 4,886,742 | 12/1989 | Kortright et al. | |
| 5,075,214 | 12/1991 | Connor et al. | |
| 5,139,744 | 8/1992 | Kowalski . | |
| 5,355,304 | 10/1994 | Demoranville et al. | |
| 5,366,896 | 11/1994 | Margrey et al. | 436/48 |
| 5,571,798 | 11/1996 | Harmenberg et al. | |
| 5,631,844 | 5/1997 | Margrey et al. | |
| 5,669,877 | 9/1997 | Blomquist | 604/67 |
| 5,730,938 | 3/1998 | Carbonari et al. | |

FOREIGN PATENT DOCUMENTS

| | | |
|---|---|---|
| WO 87/06008 | 10/1987 | WIPO . |
| WO94/11838 | 5/1994 | WIPO . |
| WO 95/00141 | 1/1995 | WIPO . |
| WO 96/05488 | 2/1996 | WIPO . |

OTHER PUBLICATIONS

Scott P. Layne, M.D., et al., "Factors Underlying Spontaneous Inactivation and Susceptibility to Neutralization of Human Immunodeficiency Virus," Virology, 1992, pp. 695–714.

Scott P. Layne, M.D. et al., "Quantifying the Infectivity of Human Immunodeficiency Virus," Proc. Natl. Acad. Sci., vol. 86, pp. 4644–4648, Jun. 1989, Immunology.

Tony J. Beugelskijk, Ph.D. et al., "Contaminant Analysis Automation," Environmental Testing and Analysis, vol. 2, No. 2, Mar./Apr. 1993, pp. 68–76.

F.A. Settle et al., "The Contaminant Analysis Automation Project," American Laboratory, Apr. 1995.

"The Contaminant Analysis Automation Project," Los Alamos National Laboratory, Apr. 1995, pp. 1–15.

T. J. Chahil, et al., "Data Acquisition in the Viral Serology Laboratory for Clinical Decision Support in AIDS Research", Proceedings of the 1994 20th Annual Northeast Bioengineering Conference, Mar. 17–18 1994, Springfield, MA, US, pp. 111–112.

Copy of International Search Report dated Apr. 14, 1998 from corresponding PCT application Serial No. US987/22732 filed on Dec. 8, 1997.

T.J. Beugelsdijk et al. "The Standard Laboratory Module . . . Laboratory" Chemometrics and Intelligent Laoratory Systems 21:207–214 (1993)(Exhibit 7).

(List continued on next page.)

*Primary Examiner*—Thomas Peeso
*Attorney, Agent, or Firm*—Merchant, Gould, Smith, Edell, Welter & Schmidt

[57] ABSTRACT

A method and apparatus for sharing integrated testing services with a plurality of autonomous remote clients is disclosed. In the disclosed method, in response to an access request message, a process controller transmits an access enabling message to the remote client. The access enabling message includes instructions performable by a remote client to generate test equipment commands. A process controller interprets and transforms these commands into automated test instrument suite commands, which are provided to laboratory modules to perform the indicated tests. Test data results are then obtained and transmitted to the remote client.

39 Claims, 12 Drawing Sheets

OTHER PUBLICATIONS

J. Gentsch, "Flexible Laboratory Automation to . . . 90s" Chemometrics and Intelligent Laboratory Systems 21:229–233 (1993)(Exhibit 8).

T. Ikeda & F. Takahata "Total Clinical Laboratory . . . Automation" Hitachi Review 41(4) (1992) (Exhibit 9).

PCT International Search Report, PCT/US 97/22543 dated May 12, 1998 (Exhibit 10).

Larger fraction    Infectious    Smaller fraction
                   Noninfectious New particle Shedding of gp120
Loss of reverse transcriptase

METHOD AND APPARATUS FOR GLOBALLY-ACCESSIBLE AUTOMATED TESTING

GOVERNMENT LICENSING RIGHTS

The U.S. Government has a paid-up license in this invention and the right in limited circumstances to require the patent owner to license others on reasonable terms as provided by the terms of Grant No. 009634 awarded by UC Los Alamos National Scientific Lab.

CROSS REFERENCE TO RELATED APPLICATIONS

This application is related to the following, which are hereby incorporated by reference:

application Ser. No. 08/763,222 entitled "APPARATUS FOR TESTING FOR INFECTION BY A RETROVIRUS," by Scott P. Layne, M.D., and Tony J. Beugelsdijk, Ph.D., M.B.A., and assigned to the assignee of this application; and application Ser. No. 08/764,721, entitled "APPARATUS FOR AUTOMATED TESTING OF BIOLOGICAL SPECIMENS," by Scott P. Layne, M.D., and Tony J. Beugelsdijk Ph.D., and assigned to the assignee of this application.

BACKGROUND OF THE INVENTION

The AIDS epidemic is a world wide problem. Over the past three decades, HIV infections have risen from sporadic cases to a global pandemic involving more than 18 million individuals. In 1995 alone, end stage infections (AIDS) killed one million individuals, making it the world's sixth largest leading cause of death by infectious disease. Even worse, all indicators suggest that AIDS deaths will continue to climb in this ranking. An estimated seventy-five percent of the world's new infections are attributable to sexual transmission, making it imperative that we understand the virologic factors influencing the pandemic.

Investigations have shown that HIV mutates very rapidly—as much as 10 to 50 times faster than an influenza virus. Further, some of the most virulent strains of HIV are appearing in remote corners of the globe. For example, HIV-1 strains have been observed in Thailand which appear to be more infectious than the more common HIV-1 strain prevalent in the western world.

There are no vaccines to prevent the spread of an HIV infection and their timetable for development is uncertain. Antiviral drugs (such as AZT and the latest protease inhibitors) may help to prolong the lives of infected individuals (or increase their quality of life) but they have no impact on preventing new infections. Much progress has been made in identifying host HIV infection spreads (sexual intercourse, mother to child, needle sharing by drug users, and blood transfusions) and in launching public health programs to reduce these modes of transmission. But the important strides made thus far in controlling the epidemic may ultimately be limited by HIV's apparent ability to mutate rapidly and to increase its transmissibility.

The spread of HIV depends on the behaviors and interactions of people as well has the inherent transmissibility of the virus. In developed countries, epidemiological studies show that the risk of person-to-person transmission ranges from one to five new infections per 1000 sexual encounters. In developing countries like Thailand, more recent epidemiological studies suggest that the risk of transmission is one order of magnitude greater—ten to fifty new infections per 1000 encounters. Attempts to attribute this increased transmission to known HIV risk factors such as the numbers of sexual partners, frequency of encounters, varieties of behavior, amounts of drug use, and prevalence of sexually transmitted diseases have revealed no clear connection. The world is thus confronted with the worrisome possibility that certain HIV isolates are appearing which are more transmittable than others. This is accompanied by reports of a rapidly growing HIV epidemic in Thailand, which now appears to involve viral isolates that belong to particular genetic subtypes.

Thus far, research on HIV has focused on its genetic and immunologic properties. The RNA genome within HIV mutates very rapidly, primarily due to the error-prone activity of reverse transcriptase. This enzyme produces nearly one base substitution per 3000 nucleotides, which means that each newly transcribed virus contains several mutations in its 10,000-base genome. The high mutation rate has produced countless numbers of HIV variants and, as time passes, it is feasible that more transmissible viruses may appear in concert with accelerating epidemics. This may help to explain the explosive HIV epidemic in Thailand.

Studying the RNA message within HIV has resulted in the cataloguing of thousands of HIV sequences in the Human Retrovirus and AIDS Database. At present, there are at least eight sequence subtypes for HIV-1 (designated by the letters A, B, C and so forth) and, given more limited data, there appear to be at least two for HIV-2. Each subtype has a characteristic phylogenetic map and differing geographic distribution, making it possible to track the evolution of the epidemic. The total number of sequences that may fit into a particular subtype, however, is truly enormous. For example, assuming that HIV is limited to utilizing just 2 different amino acids at certain positions within its proteins and that a "model" subtype is determined by substitutions in 30 independent positions (or approximately 1% of the 3000 amino acids in HIV's entire genome), the model subtype could contain as many as $2^{30}=10^9$ different sequences—an insurmountable number even if only a small set of all possible combinations produced active viruses. Given the difficulty of sequencing thousands of HIV isolates in their entirety, it seems improbable that current technologies will enable identification of genetic sequences that correlate reliably with transmissibility. In other words, certain subtypes may act as surrogate markers of transmissibility but may not identify the underlying mechanisms.

Serotyping HIV isolates is being carried out currently with standardized panels of immunoglobulins that block the virus from infecting of $CD4^+$ cells. This often used approach has allowed virologists to categorize isolates according to their patterns of susceptibility and to target certain HIV serotypes for vaccine development. Susceptibility to blocking, however, varies markedly with (even) single amino acid substitutions within the gp120 envelope glycoprotein. Consequently, the enormous combinatorics and limitations on sampling has restricted our ability to identify serotypes that correlate reliably with transmissibility.

Epidemiologists are using increasingly convenient tools to conduct rapid field surveys of HIV prevalence and the incidence of new infections. Newer methods use body fluids such as saliva (instead of blood) to determine whether individuals are HIV infected. Because this reduces the physical invasiveness of sample collection, it often increases the willingness of individuals to participate in epidemiological surveys. These innovations, together with various types of mathematical models, permit epidemiologists to track and analyze the HIV epidemic with increasing accuracy. The necessary tools are available for conducting repeated estimates of person-to-person transmissibility and matching them with the physical properties of HIV isolates.

As the above demonstrates, there is a need for new measurement-based schemes that integrate epidemiologic, immunologic and virologic data to understand why more transmissible HIV isolates may be emerging. Unfortunately, this need is difficult to meet for two reasons. First, many of the newer strains of HIV and other infectious diseases are emerging in remote areas of the world where laboratory facilities are simply non-existent. Second, many of the tests which need to be performed to gather the necessary data require an overwhelming number of repetitive operations and a biohazard safe environment.

Current automated laboratory instruments have not been up to the task. These special purpose, automated laboratory instruments have been designed to imitate human actions as closely as possible. A control program directed robotic hands on tracks to shuttle samples from one location to another, and also commanded the same hands to carry out elementary operations. The number of operations determined the number of stations, and procedures were completed when samples reached the end of the machine. These forerunners of today's automated instruments were simple in concept but they also had drawbacks. Their mechanisms were easily overloaded by too many elementary operations and, due to this restriction, overall utility was rather limited. Furthermore, small mechanical glitches (such as the mishandling of samples) often precipitated crashes, necessitating time-consuming interventions by trained technicians.

In recent years, stations performing only one elementary operation have given way to "standard laboratory modules" (SLMs) that integrate several operations into one logical and coherent task. This newer type of design has noteworthy advantages. For example, it distributes work that is ongoing within the instrument among several semi-autonomous units. Placing two or more identical SLMs within the same instrument is analogous to adding extra processor chips to parallel-processing computers—it eliminates bottlenecks and speeds up critical tasks. Decentralization of tasks in SLM-based instruments reduces the number of operations performed by robotic hands, allowing them to act mainly as transporters which markedly increasing instrument flexibility and reliability. SLMs are more easily reconfigured to perform a wider variety of tasks to a wider variety of potential users than special purpose robotics.

However, SLM technology alone is insufficient to meet emerging data acquisition and analysis needs. While SLMs can be applied to broader ranges of experiments, their flexibility remains limited. Further, SLM technology is available only to a small number of research scientists, and will likely remain so because of cost and logistical constraints. In light of the above, it is apparent that there is a need for an integrated SLM technology that provides a broad range of services to the scientific community, especially those adaptable to solve rapidly evolving test analysis problems.

SUMMARY OF THE INVENTION

The present invention offers a unique solution to above-described problems by providing a method of sharing integrated testing services with at least one autonomous remote client. The method comprises receiving an access request message in a process controller communicatively coupled to an automated test equipment suite. The process controller responds with an access enabling message, typically comprising computer instructions which allow the remote user to directly or indirectly command the instruments in the automated test instrument suite. The remote client uses these instructions to generate test command messages which are sent to the process controller where they are interpreted to define task sequence controller commands. The task sequence controller then uses these commands to generate specific events and configurations for standard laboratory and support modules, which perform the indicated tests and measure the results. These results are then made available to the remote client, and if the remote client desires, to others with similar access to the automated test instrument suite on a selective basis.

BRIEF DESCRIPTION OF THE DRAWINGS

FIG. 1 is a diagram showing the three interrelated AIDS research disciplines.

FIG. 2*a* is an illustration of the release of newly manufactured HIV particles from $CD4^+$ cells;

FIG. 2*b* is an illustration of the spontaneous loss of HIV infectivity by viral degradation processes;

FIG. 3*a* is an illustration of how the reproductive number influences the growth of viral infection;

FIG. 3*b–c* is an illustration of how steady kinetics govern viral loads in vivo;

FIG. 4 is an illustrative overview of the remote automated testing of the present invention;

FIG. 5 is a block diagram of one embodiment of the remote automated test apparatus;

FIG. 6 is a diagram illustrating the process control tools of the present invention;

FIG. 7 is a diagram illustrating the processes performed by an "infectron";

FIG. 8 is a diagram showing one embodiment of the infectron of the present invention;

FIG. 9 is a diagram illustrating the processes performed by a "detectron"; and FIG. 10 is a diagram showing one embodiment of the detectron of the present invention;

FIG. 11 is a flow diagram of the method steps employed in one embodiment of the present invention; and FIG. 12 is a flow diagram of the method steps employed by the remote client.

DETAILED DESCRIPTION OF THE PREFERRED EMBODIMENT

1. Integrated Phenotypic Studies of the HIV Virus

FIG. 1 is a diagram summarizing the interdisciplinary approach required to solve the HIV puzzle. As described herein, current efforts have focused on epidemiological surveys and genetic sequences. Epidemiologic surveys determine the modes of HIV transmission (i.e., sexual, maternal-child and drug use), estimate of person-to-person transmissibility and relate transmissibility with viral loads in vivo. Genetic sequences studies classify HIV by viral subtypes, provide geographic perspectives on the epidemic, and track HIV-RNA evolution over time. As described earlier, the difficulty in sequencing and assaying thousands of HIV isolates in their entirety is problematic and has proved problematic to AIDS research efforts, and the rapid mutation capability may render these efforts ineffective.

The present invention uses an integrated approach whereby these epidemiological and genetic efforts currently underway are integrated with studies of the phenotypic properties of HIV. Understanding phenotypic properties and their associated extracellular reactions, which take place simultaneously as HIV particles diffuse and attach to uninfected cells, lends additional insight into the complementary array of intracellular reactions. These phenotypic or physical properties (measured by quantitative viral infectivity assays) characterize the chemical and kinetic behaviors of HIV particles, such as infectious fractions, spontaneous decay rates and reproductive numbers. FIG. 2 and FIG. 3 illustrate these HIV particle properties. Other phenotypic properties of HIV particles are also of interest, including those related to the virus's immunologic, physical-chemical and enzymatic characteristics.

Figure 2A:
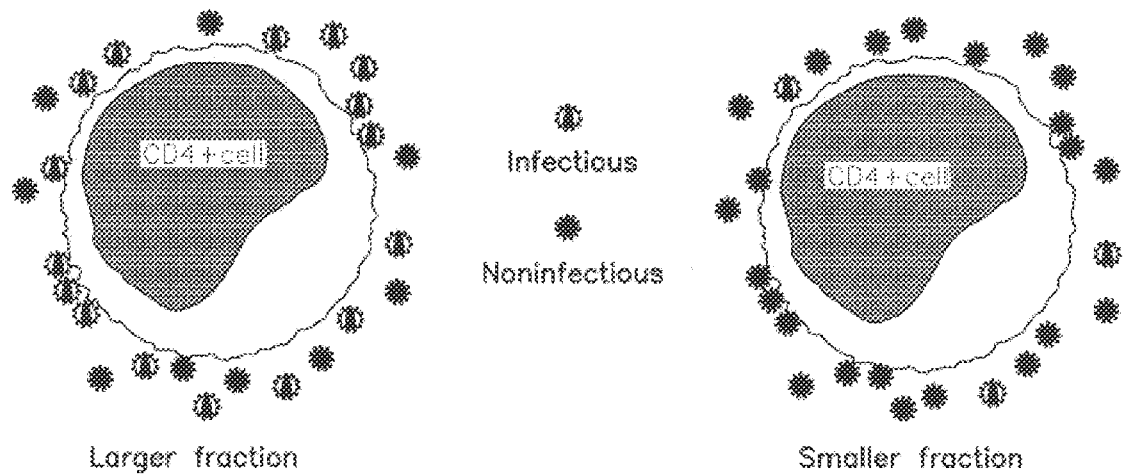
Figure 2B:
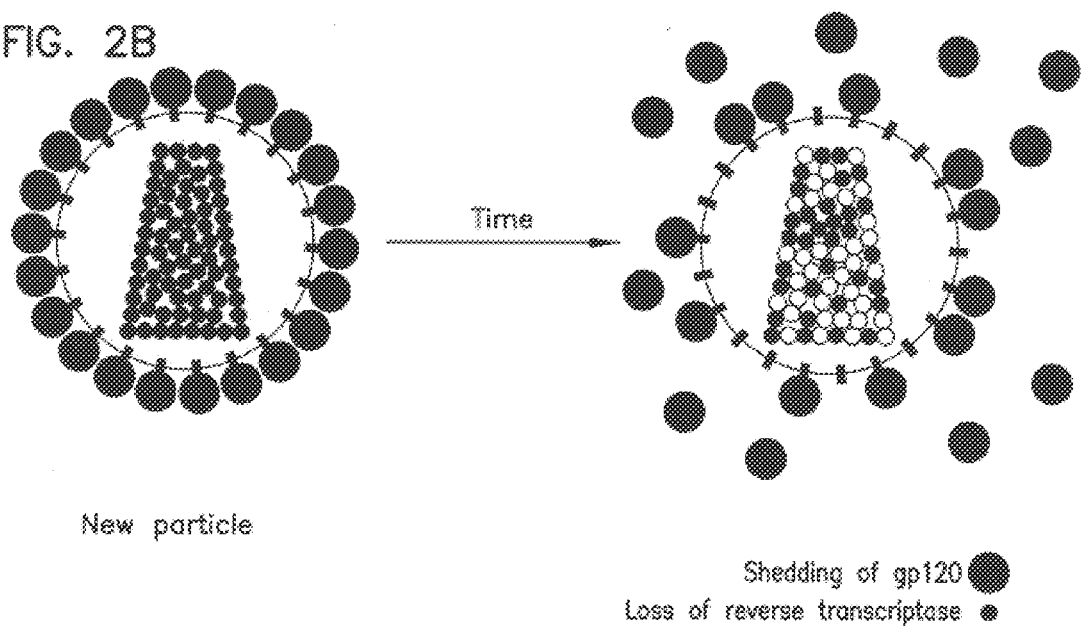

FIG. 2a illustrates the release of newly manufactured HIV particles from $CD4^+$ cells. Experiments with one strain of virus (HIV-1HXB3) have demonstrated that a very small fraction (<0.01%) of these particles are infectious. More transmissible HIV isolates may have larger infectious fractions compared to less transmissible ones. FIG. 2b illustrates the spontaneous loss of HIV infectivity. With time, gp120 complexes fall off the virus and reverse transcriptases lose their enzymatic activity. Both molecules are believed necessary for maintaining infectivity—gp120 initiates viral entry by binding to CD4 receptors on cell surfaces and reverse transcriptase initiates replication by converting RNA to DNA. More transmissible HIV isolates may have slower rates of decay compared to less transmissible ones.

Figure 3A:
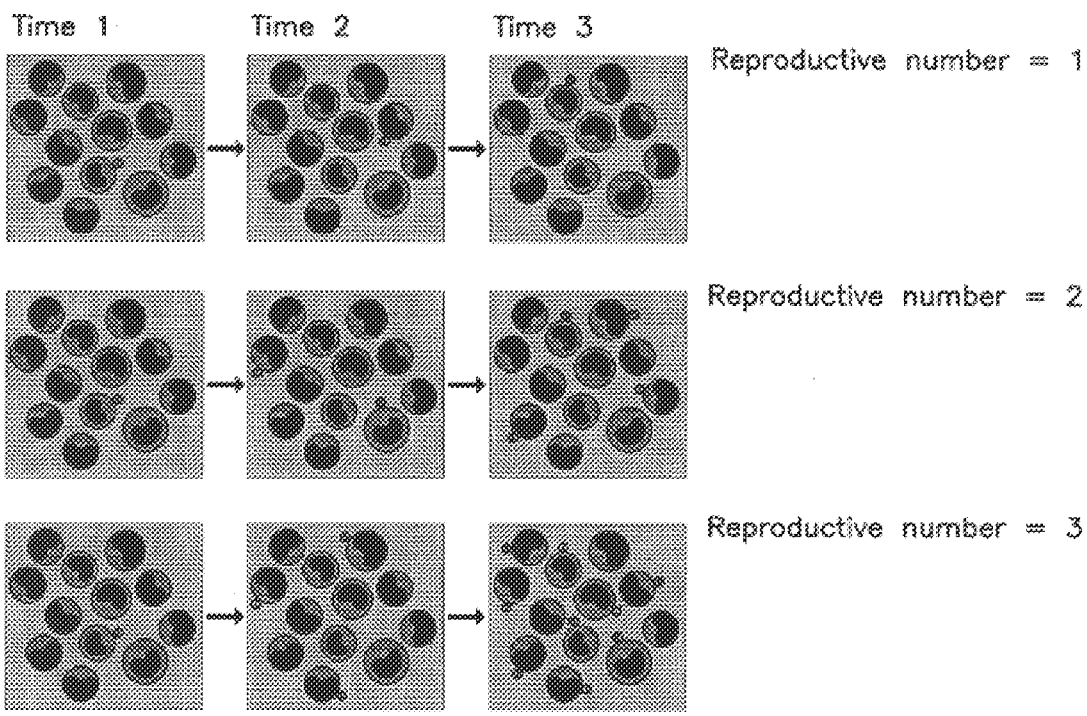

FIG. 3a. illustrates how the reproductive number influences the growth of viral infection. Each infected $CD4^+$ cell manufactures a certain number of virions—the reproductive number—that diffuse and infect neighboring susceptible cells. This viral "chain reaction" is shown for three time cycles and three different reproductive numbers. At time 1, all boxes contain one infected cell. A reproductive number of one leads to a constant burden of infected cells. A reproductive number of two leads to infections that double per cycle, and a reproductive number of three leads to infections that triple per cycle. Reproductive numbers greater than one thus lead to infections that grow exponentially with time. More transmissible HIV isolates may have greater reproductive numbers compared to less transmissible ones.

Figure 3B:
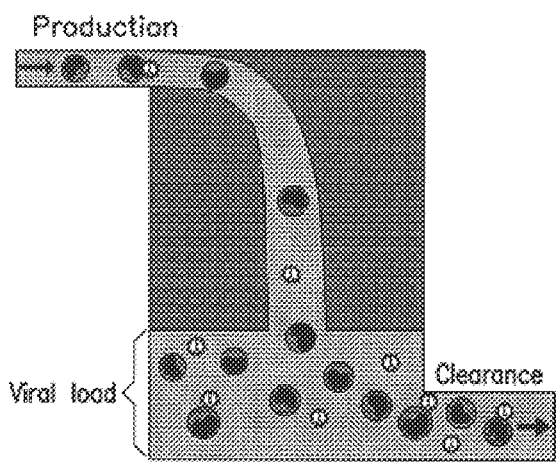
Figure 3C:
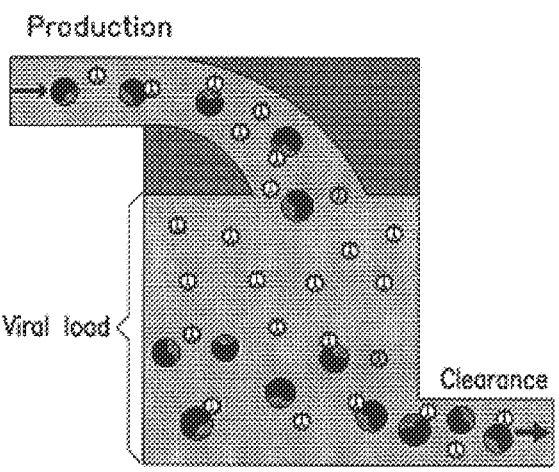
Figure 4:
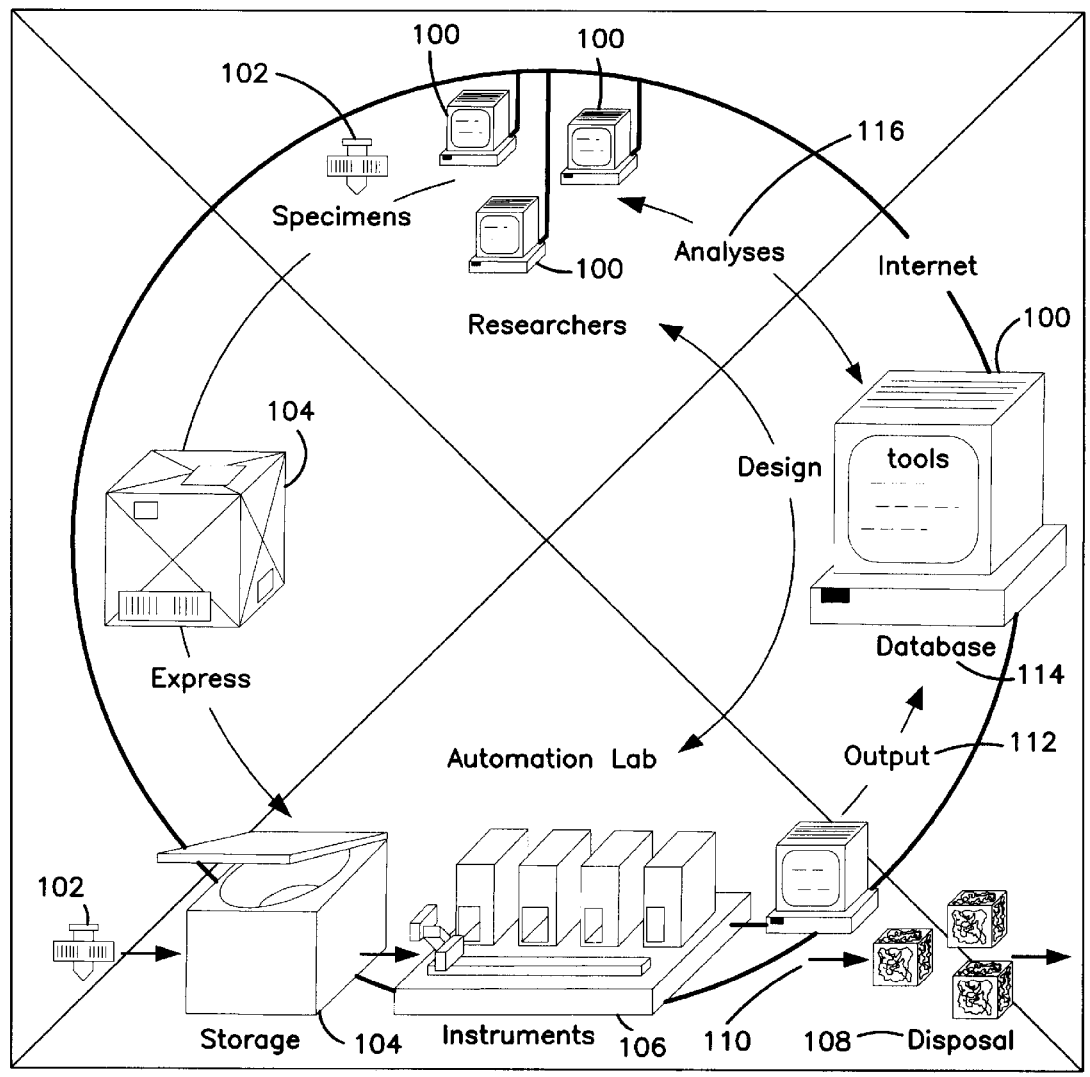
Figure 5:
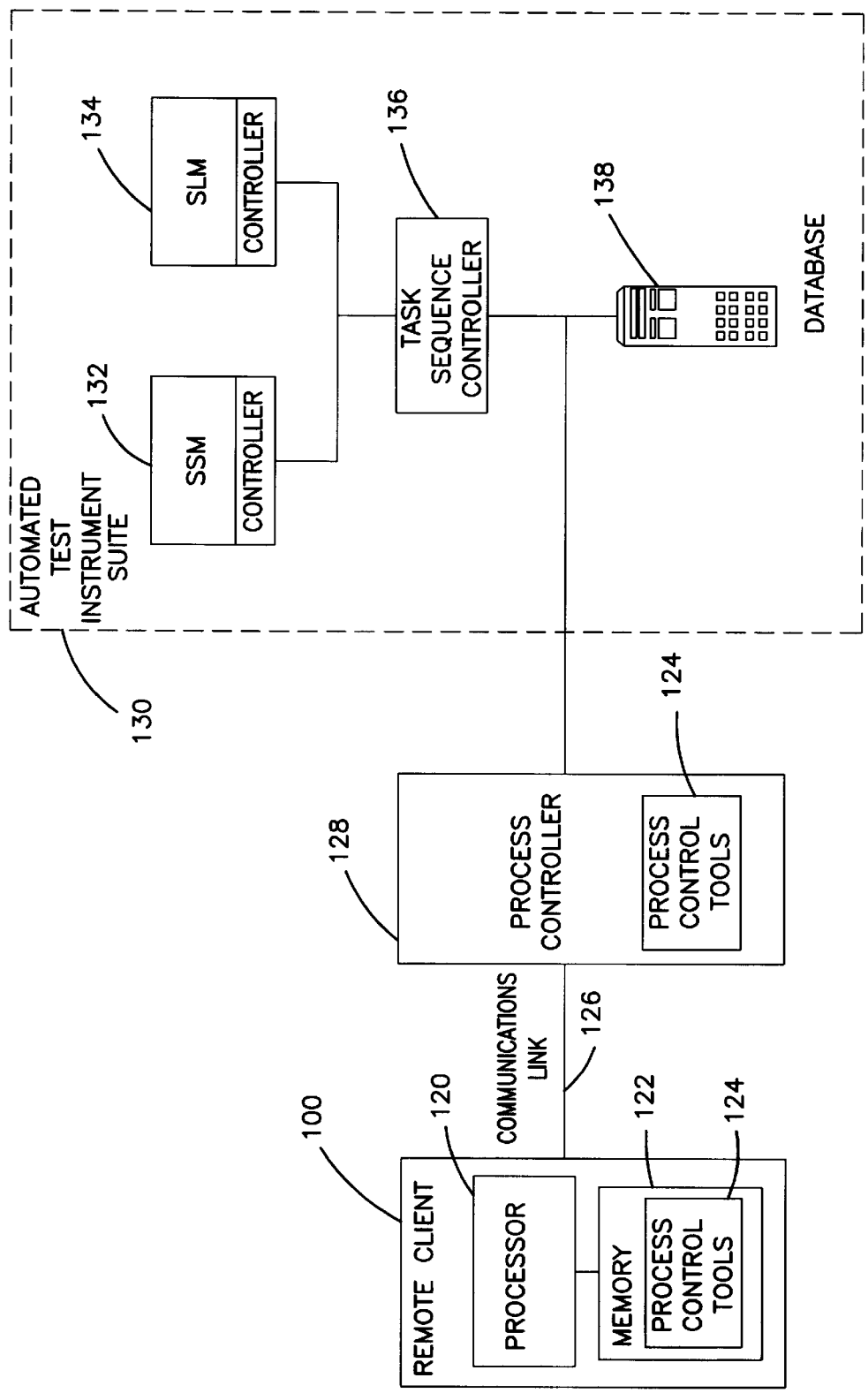

FIG. 3b illustrates how steady-state kinetics govern viral loads in vivo. Viral production by $CD4^+$ cells is represented by liquid pouring into the cistern and viral clearance by the immune system is represented by liquid pouring out. Over time, the viral load (represented by the liquid's height) builds up to a level where the total input matches the total output. Both cisterns have similar rates of clearance but the cistern on the right has a greater rate of production. Consequently, the viral load is much greater in this cistern. More transmissible HIV isolates may have greater rates of viral reproduction in vivo which generate larger viral loads.

Quantitative viral assays have demonstrated that a rather small fraction of HIV particles is capable of infecting $CD4^+$ lymphocytes. Based on in vitro experiments, with a molecular clone called HIV-1HXB3, this fraction varies from one infectious particle per $10^4$–$10^6$ virions. The small number for one viral isolate raises the question of whether more transmissible isolates have significantly larger fractions of infectious particles, as described with respect to FIG. 2a. It also raises the question of how the "infectious fraction" varies with the type of target cell. For instance, certain HIV-1 isolates from Thailand (belonging to subtype E) appear to be transmitted heterosexually, whereas other isolates (belonging to subtype B) appear to be transmitted mainly by intravenous drug use. Subtype E isolates have been found to exhibit a pronounced tropism for CD4+ Langerhans cells derived from human vaginal mucosa and penile foreskin. These macrophage-like cells reside just below the epidermis, so small abrasions in the skin may provide an efficient entryway for HIV infection. The relationship between these isolate and tropism variates and infectious fraction measurements is a promising research topic, but has not been fully explored. This is due to the lack of relevant data, which, in turn is due to the unavailability of lab instruments capable of performing these experiments rapidly. The same is true for quantifying the relationships between isolate and tropism variations an infectious fraction. Similarly, these isolate and tropism variations should be examined and related to infection fraction measurements. Also, laboratory methods for quantifying the infectious fraction should examine these isolate and tropism variations.

The relationship between the infectious fraction and the amount of contaminated blood that remains in drug users' syringes should be examined. However, these measurements are labor intensive and the subtype E HIV-1 isolates are typically found in areas of the world where laboratory experiments cannot be performed. Accordingly, research into this promising area has not progressed.

Newly manufactured HIV particles start out with about 80 gp120 receptor complexes on their surface and 100 active reverse transcriptase molecules in their core. As shown in FIG. 2b, over a period of several hours, the gp120 complexes spontaneously fall off the virus and the reverse transcriptases lose their enzymatic activity. These proteins are believed necessary for maintaining viral infectivity and their continual disappearance results in the stepwise loss of HIV infectivity. Spontaneous degradation is an intrinsic "physical property" of HIV, raising the issue of whether more transmissible isolates have slower rates of decay. Together, these observations demonstrate that HIV has several ways of modulating its infectivity. They may act alone or in concert to affect person-to-person transmissibility.

When HIV-infected mothers deliver, the barriers between maternal and fetal circulations naturally break down. At birth, newborns are exposed directly to their mothers' blood, causing HIV transmission in nearly 25% of the time. When antivirals such as AZT are given to expectant mothers, their CD4+ cells produce lesser amounts of HIV and blood concentrations of cell-free virus fall by several fold. Consequently, newborns are exposed to smaller quantities of HIV and transmission declines to about 8% of births. Based on these outcomes, clinical trials with other potent antiviral agents have been initiated, which promise to reduce the probability of neonatal transmissions even further.

The factors influencing the spread of HIV from mother to infant may provide crucial insights into other modes of transmission. Associations between transmissibility and viral load suggest, in general, that more infectious individuals carry greater loads in their circulation. The analyses of antiviral drug trials by mathematical models demonstrate that in vivo concentrations of HIV obey so-called "steady-state" kinetics, where clearance of infection by the immune system matches ongoing viral replication. This kinetic behavior means that HIV isolates with larger "reproductive numbers"—the total number of infecting virions generated by each infected cell—generate correspondingly larger viral loads and vice versa, as depicted in FIG. 3a. Infected individuals also harbor genetic swarms of HIV isolates in their blood called "quasispecies" which possess closely related genotypes yet can exhibit broadly divergent phenotypes. Each unique member of this quasispecies may have different reproductive numbers, cellular tropisms and immune clearance rates. With these dynamic relationships, it is conceivable that viral loads and reproductive numbers may act alone or in concert to affect person-to-person transmissibility.

Extracellular reactions determine the infectivity of HIV particles and their susceptibility to blocking by humoral agents (such as soluble CD4, monoclonal and polyclonal immunoglobulins). These reactions also determine the infectious stability of HIV particles and the absolute fraction of infectious particles.

The infectivity of HIV particles is proportional to the total number of glycoprotein 120 molecules (an HIV attachment protein herein after referred to as gp120) in the virus's envelope. A virion with 80 gp120 molecules is twice as infectious as one with 40 gp120s and so forth. Because of this phenotypic property, the blocking activity of immunoglobulins (i.e., their biological titer) is related inversely to the density of $CD4^+$ cells. At relatively low CD4+ cell densities, like those found in blood, immunoglobulins are able to block infection. Whereas at higher cell densities, like those found in inflamed genital ulcers and lymph nodes, the same immunoglobulins are much less able to block. This finding has relevance for developing effective vaccines and understanding viral pathogenesis. It suggests that vaccine-induced immunoglobulins will offer reduced benefits for certain populations with sexually transmitted diseases. It also suggests that immunoglobulins will offer reduced blocking activity for infections that are invading lymph nodes. It appears that immunoglobulins must block HIV at an earlier stage of infection.

Other phenotypic properties are likely related to immunity, transmissibility and viral loads in vivo. Thus, in addition to genotypic properties, experimentally measurable phenotypic properties provide equally important (and unique) information on HIV. Expanding basic-science investigations on HIV phenotypes will promote development of HIV therapies.

2. Automated Remote Testing Services

As described above, a systematic survey of HIV's biochemical and biophysical parameters (including its infectious fraction, gp120 shedding, reverse transcriptase loss and reproductive number size) would generate valuable information that is useful in two respects. First, it proves new information regarding how physical properties vary from virus to virus. This would permit estimates of the range and distribution of these properties for all isolates. Second, it provides information on the bulk behavior of the virus. This type of "macroscopic" data would complement the more "microscopic" data that has been obtained from the study of HIV's molecular genetics. This systematic survey would answer several basic questions about HIV viruses around the world. For example, for each physical property of HIV, these tests will identify the entire spectrum of behavior such as the highest and lowest infectious fractions or the slowest and fastest rates of decay. These tests will also determine where viruses from various geographic regions rank in this overall spectrum and how person-to-person transmissibility relate to this ranking.

Virologists have developed reliable and quantitative assays of HIV's physical properties. The present invention uses assays which use human cells that support the growth and detection of wild-type viruses. These include peripheral blood mononuclear cells (PMBCs), monocytes/macrophages, and Langerhans cells. This highly flexible assay format uses "target cells" and "indicator cells." Unfortunately, measurements of HIV's physical properties using assays have been repeated for only a small number of isolates. This is because these assays, like many others, require labor intensive processes, posing a major obstacle to their widespread use. For instance, measuring HIV's spontaneous decay requires data collection around the clock for several days. Decay assays must then be analyzed and repeated several times, amounting to a substantial amount of work . . . all for just one viral isolate. It is little wonder that HIV's physical properties have been reported for only a small number of isolates. Conventional biohazard laboratories are methodologically rich, yet also technician time and labor poor. This situation is made worse by the geographic spread of the HIV virus. Many viral strains are prevalent in locations where access to laboratory materials and procedures is limited or impossible, especially for a rapidly mutating virus such as HIV. There is therefore a need to provide remote automated testing and analysis capability to research scientists and other users around the globe, and to provide the means to disseminate and perform analysis on this data. The present invention meets this need.

FIG. 4 presents an overview of the remote automated testing apparatus and method of the present invention. The present invention allows researchers with access to remote client computers or processors 100 can perform automated testing on specimens 102. Using the internet or other communication link capability, the remote user sends a message via a remote client 100 to request access to the services provided by the automated lab. If access to the automated lab is granted, a message is sent to the remote client computers 100. Included with this message are instructions enabling program control tools which allow the remote user to define and perform the automated tests. If the desired tests require the submission of test specimens 102, the program control tools are also used to define the requirements for packaging and labeling these specimens 102. Using the communications link, the remote user then communicates with the remote lab to design the experiments to be performed. If required, specimens 102 are then packaged 104 and physically transported to the automated lab site via commercially available carriers. When the packages arrive, the automated lab places them in storage 104 as directed, or until the tests are scheduled to be performed. Automated instruments 106 perform the tests specified by the remote user, arrange for the disposal of waste materials 108, and the test results, or output 112 is provided to the remote user. If desired, the remote user can arrange to have the data stored in a database 114, where it may be made available to other remote users, according to the submitting remote user's wishes. The remote user can also use the program control tools to perform analysis on the test data generated by the submitting user or other users.

FIG. 5 is a block diagram depicting one embodiment of the present invention. The automated test instrument suite 130 comprises a plurality of standard modules 132 and 134. These modules include one or more standard laboratory modules (SLMs) 134 and one or more standard support modules (SSMs) 132.

Standard laboratory modules are logical groupings of laboratory unit operations (LUOs) which perform a subtask of an analytical protocol. SLM boundaries are by no means easy to identify, but logical groupings of LUOs comes from the suite of analytical methods performed in the laboratory. When looking at a large number of these methods, all of which feed a common analytical finishing technique, the methods converge in terms of the operations. Commonality among methods at this point serves as guidance for the SLM boundary selection.

Other SLM boundary selection considerations include the complexity and time required to perform the operation. For example, if the operation can be completed relatively quickly it is ordinarily too time consuming and inefficient to cast the operation in a separate piece of hardware. It is important to avoid such rate-limiting SLM boundary selections. Also, ordinarily, no SLM needs or has "knowledge" of another SLM. This function is handled by the task sequence controller. Instead, a given SLM merely announces its state, whether available, busy, finished, initializing, in trouble or otherwise. An SLM is therefore effectively a machine that responds to a finite number of states.

SSMs 132 provide transport modality or other means for moving objects within the system. This includes taking specimens from storage 104, preparing them, making them available to SLMs 134, removing specimens and eliminating waste.

SLMs 132 have knowledge of the availability of the SSMs 132. For example, a SLM 134 "knows" whether there are enough specimens or other materials for it to function. This is because before the SLM can be directed by the task controller to perform a function, it first must ascertain whether it has enough materials to complete the task. The SLM 134 checks the SSM 132 tasked with providing the materials, and either proceed or report that it cannot do so and state a cause.

Both the SLMs 134 and the SSMs 132 have low-level controllers which drive components like actuators, detectors, and servomotors. The controllers also coordinate the internal electromechanical activities of the SLMs 134 and SSMs 132. Controllers also comprise software packages that provide a menu of programmable "configurations" and each one of these "configurations" corresponds to a customized task carried out by the module. For example, in liquid-dispensing SLMs, a configuration may supply fresh tubes, adding several aliquots of reagent to each, and capping them afterwards. In centrifuge modules, a configuration may specify the loading of tubes, delivering g-forces for a specified time (nominally 1000 g for one minute), and unloading them after the spin. Programmable configurations are defined by certain physical parameters (volumes, g-forces, times, temperatures, etc.) and well-designed controllers disallow situations that are operationally improper, such as overfilling tubes and centrifuging upside-down tubes. For AIDS research, certain high-level tools could program SLM controllers dynamically, enabling one instrument to perform any number of unique assays.

The SSMs 132 and SLMs 134 are communicatively coupled to one or more task sequence controllers 136. Task sequence controllers (TSCs) 136 are intermediate level devices which use tools from operations research to govern intricate flows of supplies and samples through automated instruments. Before performing actual tests, computer simulations mimic SLM 134 controllers and adhere to critical timing events of the candidate tests procedures. This virtual instrument then generates start-up times and optimizes the sequence by which all tasks take place. TSCs users include laboratory technicians who load materials into automated instruments and supervise their performance on a daily basis (complete runs can amount to ~10,000 tasks, for example, which far surpass the manual scheduling capabilities of humans) and engineers who develop and debug new instruments or look for ways to improve on existing ones. TSCs 136 are capable of dynamic retasking, which, for example allows adding and subtracting assays while automated instruments are up and running—a particularly useful feature for clinical work.

The task sequence controller 136 is communicatively coupled to a process controller 128. The process controller 128 interfaces between the remote client and the automated test instrument suite 130, providing level process control tools 124 to remote client 100. These process control tools are the front line communication and management tools which provide the interface between remote users and the automated test instrument suite 130. The process control tools 124 also allow the remote client 100 to access, control, and process data in database 138, thus influencing the ways in which researchers carry out their test activities as well as collaborate with others. Computer instructions implementing the process control tools 124 can be shared between the process controller 128 and the remote client 100, but can be implemented by either alone. When the remote client 100 requests access to the automated test instrument suite 130, a portion of the instructions residing at the process controller 128 are transmitted to the remote client 100 over the communications link, 126, processed by the processor 120, and stored in the remote client memory 100. In one embodiment, the communications link 126 is the message transfer modality commonly known as the "internet." The internet is particularly suited to the application described herein since it offers global accessibility and high speed data transfer of vast amounts of information.

Once stored in the memory 122, the remote client 100 can use the process control tools 124 cooperatively with the process controller 128. In one embodiment, the process controller 128 resides on the gateway computer of the automated test instrument suite 130, and it provides process control tool enabling instructions to remote clients 100 for downloading via the Internet. By supplying necessary program instructions directly to remote clients 100 in this way, the same program control tools 124 serves local and remote users alike.

Figure 6:
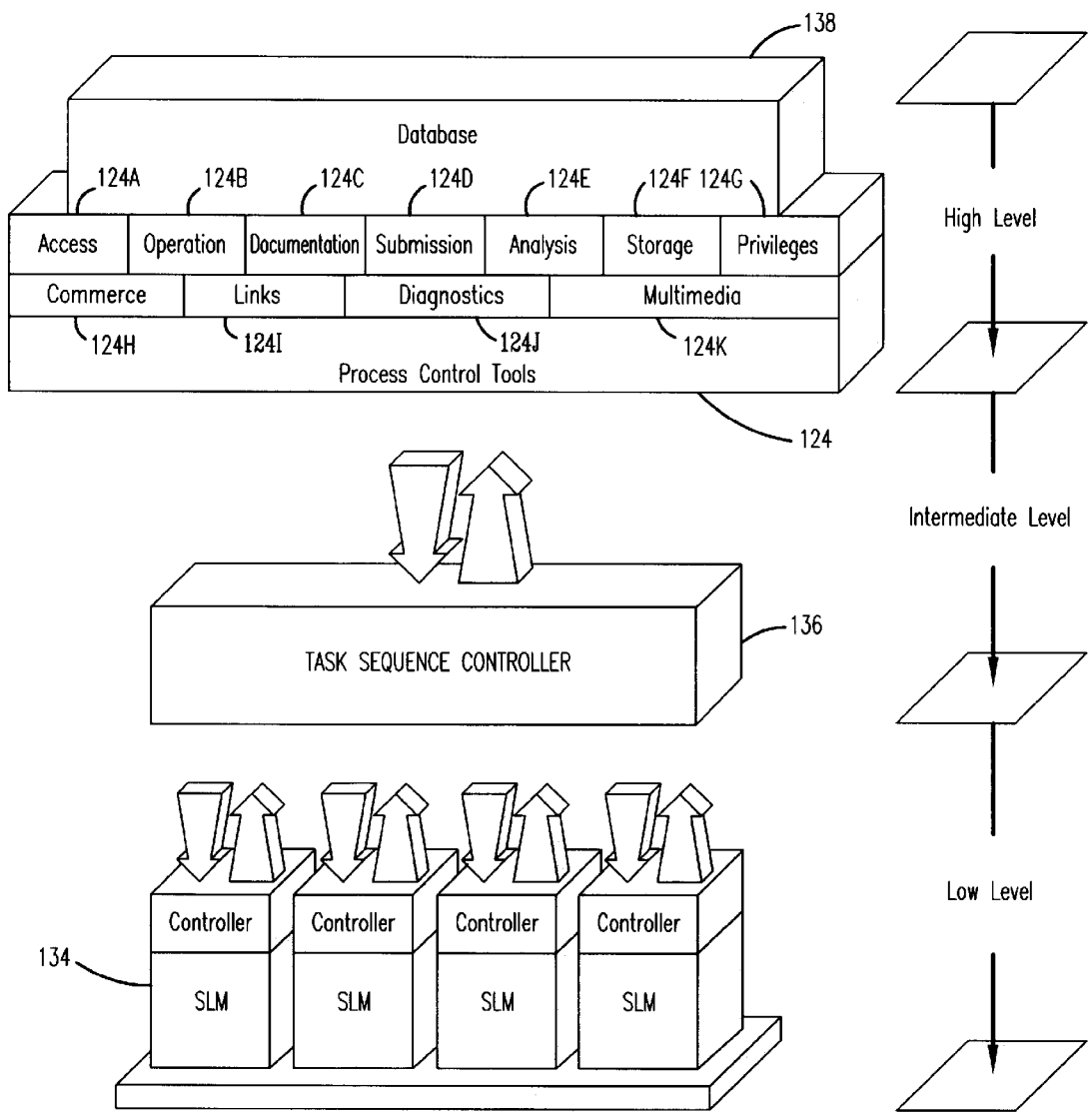

FIG. 6 presents a diagram showing the process control tools 124 and how they relate to other elements of the present invention. The process control tools (PCTs) 124 comprise a plurality of functional capabilities. First, access PCT 124A performs access and access control functions.

An operation PCT 124B performs automated test instrument suite 130 operation information. This PCT 124 describe how to use the instruments in the automated test instrument suite 130, and offers selections of standardized tests. For example, if assays of biological specimens is desired, selections of standardized essays are offered. This PCT 124B also allows researchers to design new experiments, and offers the test designer specified degrees of freedom (such as volumes, temperatures, centrifuge forces, etc.) and detailed simulations to permit automated test protocols to be verified before submission.

A documentation PCT 124C performs a variety of annotating functions, enabling researchers to deposit background information regarding specimens, treating agents and other items. For example, the context of biological experiments, this PCT 124C allows the remote client 100 to store and deposit background information on viral specimens, cell cultures, and the reagents used in the assays. This PCT 124C may also be used to define how long samples have been in storage before the testing began. Data related to the documentation PCT 124C can be stored in the remote client memory 120, the automated test instrument suite database 138, both, or shared between these elements.

A submission PCT 124D stipulates to the remote client 100 how specimens must be packaged and/or labeled before they are submitted for testing. This specificity facilitates reliable processing and reduces unnecessary handling of specimens, a factor which is especially important for biohazardous materials. The submission PCT 124D also can also generate labels or identification codes to be affixed to the specimens before packing and transportation.

An analysis PCT 124E provides computational tools for analyzing raw data, relational tools for linking the raw data and processed results to other information available on the database 138, and for linking other PCT 124 information and functions. This PCT 124E also helps evaluate whether specimens and assays meet acceptable quality control standards. This is especially important in situations where archival samples are employed.

A storage PCT 124F generates electronic records regarding the sample and returns them to the submitting remote client 100. To reduce the possibility of potential loss of information, these records would also be maintained by the database 138 and include elements pertaining to the history of the sample, test protocol, documentation, submission, raw data, analysis and analysis links. For example, these records could be used to establish links between how long a subject survived with an infectious disease with genetic information about the individual.

A privileges PCT 124G allows submitting researchers to designate who has permission to view or use their data. Feasible options for these information management requirements include: access by the submitting researcher only, access by certain designated collaborators, time-embargoed data followed by wider access, and unrestricted access by all.

Commerce PCT 124H implements functions related to the business aspects of the automated test facility, including billing, inventory management of test and support materials, cost modeling, promotional and educational materials, marketing, sales, and advertising.

Links PCT 124I provides connectivity tools which link with other research facilities and databases, whether local or remotely available through a communication link.

Multimedia PCT 124K comprises tools necessary to store, manipulate, and present audio, graphical, video information. This information may include a video explaining how the test facility is used, a visual depiction of the test results, test methodology, or a comment regarding the background of the experiment, or post-experiment comments. Multimedia PCT may also implement subscription functions, so that updated test data is automatically provided to remote clients or other interested parties.

In one embodiment, these PCTs 128 would be provided in platform independent instructions taking advantage of object oriented programming and modular techniques to allow support of practically any SLM instrument, and to interface with a wide variety of remote client 100 access platforms. One candidate for the process controller 128 is a UNIX based UltraSparc 2 workstation available from Sun Microsystems.™

Figure 7:
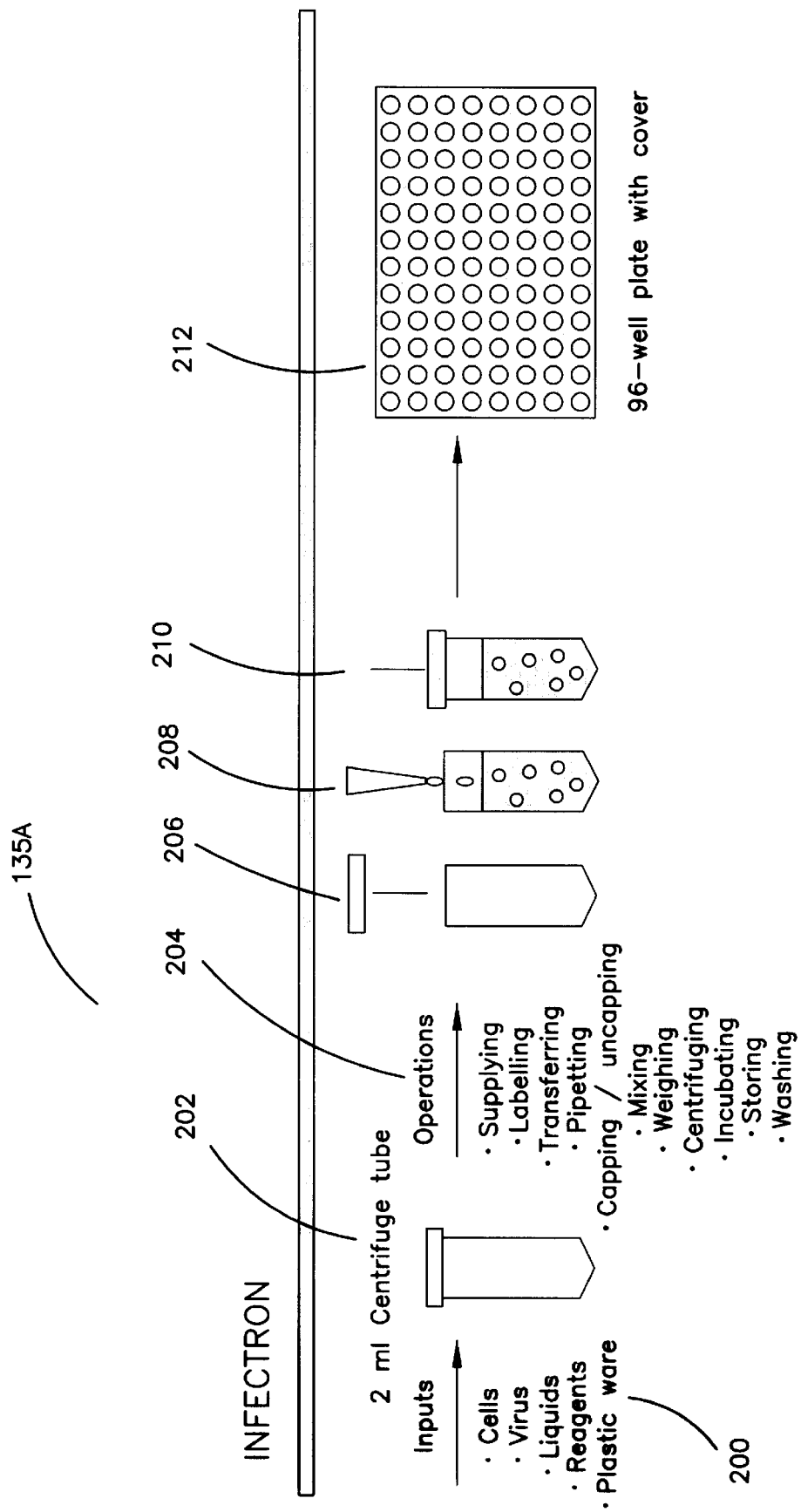

The foregoing teaching can be directly applied to an automated instrument suite for performing analytical testing of biological samples. FIG. 7 presents an overview of the process steps for performing the infection of target cells to measure HIV phenotypes. These steps are performed by a group of SLMs 134 and SSMs 132 hereinafter referred to as an infectron 135A. The infectron 135A accepts assay cells, virus samples, liquids and other reagents as well as plastic ware as inputs. Although in the normal situation, the submitting remote client provides only the virus samples, it is also envisioned that viruses, cells, liquids, reagents, and plasticware could be obtained from automated test instrument suite 130 stock supplies as well. The infectron 135A then places these items in 2 ml centrifuge tubes 202. Two ml centrifuge tubes 202 were selected to provide sufficient volume to provide a wide dynamic range of assay experiments and to simplify instrument design. In principle, any size centrifuge tube up to approximately 50 ml, or other sizes could be used.

The infectron 135A then performs a number of operations 204, including providing supply materials, labeling test samples, transferring them from storage, pipetting, capping/uncapping, mixing, weighing, centrifuging, incubating, storing, and washing the samples. When complete, the caps are again removed 206, indicator cells are added 208 and applied to a 96 well plate for further analysis.

Figure 8:
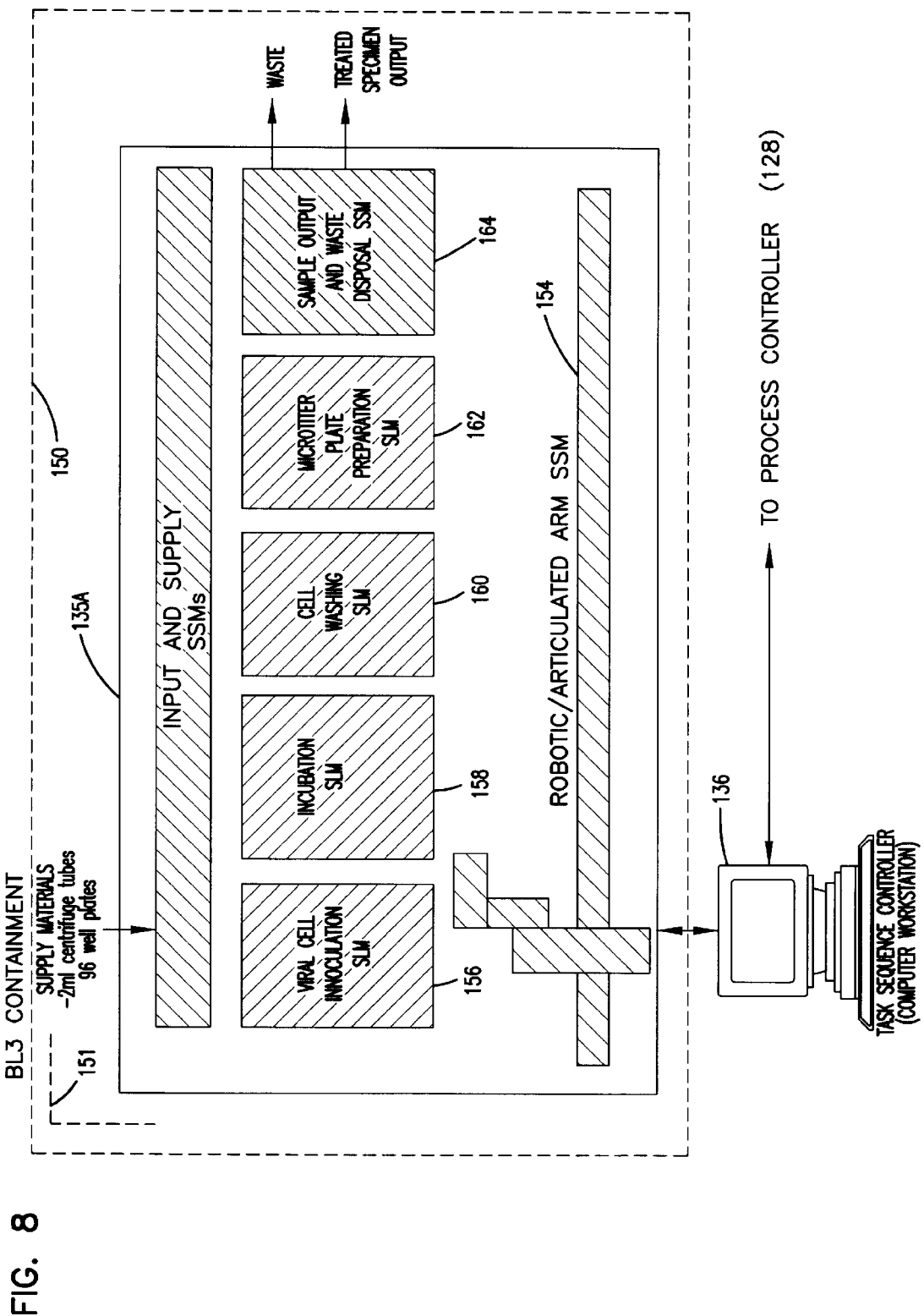

FIG. 8 further illustrates the infectron 135A operations and how a plurality of SLMs and SSMs are employed to implement these operations. Where the infectron 135A is used for testing of biohazardous materials, the it may be securely contained within a biohazard level 3 (BL3) containment facility 150. To further enhance safety, the automated instruments may be housed in customized Class I or II biological cabinets with non-recirculating air flows 151. These cabinets are designed to contain aerosols and spills, and cables, such as the electrical power and computer data cables, have hermetic seals. For simplified decontamination, hardware and housing components have no sharp parts or edges.

The infectron 135A is communicatively coupled to a task sequence controller 136, which interfaces with the process controller 128 as described above. The infectron 135A comprises an input and supply SSM 152. This module retrieves supply materials, including 2 ml centrifuge tubes and 96 well plates to the infectron 135A SLMs. In one embodiment, the input and supply SSM can be realized with only minor modifications to an SSM incorporated in the Integrated High-Density Clone-Gridding Robot developed by the Applied Robotics and Engineering Group at Los Alamos National Laboratories. Similarly, inter-SLM transport SSM 154 passes samples among the different modules. In one embodiment, the intermodule transport SSM 154 comprises a robotic/articulated arm such as the ORCA product produced by Sagian Incorporated™. These articulated arms travel along linear tracks, and have acceptable positioning tolerances, degrees of freedom and controller software for high precision manipulations.

Viral cell inoculation SLM 156 combines fresh cell cultures, liquid reagents, and viral stocks to 2 ml centrifuge tubes 202, then adds screw top caps 210. This module comprises single-tip pipette tools, tip disposal units, and integrated software for process control. In one embodiment, the viral cell inoculation SLM 156 comprises the Biomek 2000 produced by Beckman Instruments™. Capping functions can be performed by a separate capping modules if required.

Incubation SLM 158 provides a temperature controlled environment for the 2 ml centrifuge tubes 202. The temperature profile selected can be constant or varying as required. The incubation SLM 158 stores information regarding the incubation environment history, such as the time that each tube or set of tubes spends under specified incubation conditions. Commercially available instruments, such as those available from Lab-Line Instruments can perform most of the functions required, but require modification to add rotating stages for mixing 2 ml centrifuge tubes, and motorized doors for opening and closing the incubator on command. Beckman Instruments™ manufactures centrifuge motors that feasibly meet these requirements.

Cell washing SLM 160 washes infected target cells by cycles of centrifugation followed by the suspension of cells in fresh media. In one embodiment, the cell washing SLM 160 comprises a centrifuge motor with electronic radial indexing capability and a motorized lid for opening and closing the centrifuge chamber on command.

Microtiter plate preparation SLM 162 adds indicator cells, washed target cells, and liquid reagents to the 96-well plates. In one embodiment, the microtiter plate preparation SLM 162 comprises multi-tip pipette tools, tip disposal units, and storing/incubating capabilities. One possible implementation of this SLM uses a modified Biomek 2000 produced by Beckman Instruments working with test tubes and 96-well plates.

Sample output and waste disposal SSM 164 covers the 96-well plates 212 with sterile lids and store the plates in the incubator SLM 158 or elsewhere. This module, or other associated modules dispose of waste materials including contaminated 2 ml centrifuge tubes, pipette tips, cultural media, and other plastic ware and liquids.

Figure 9:
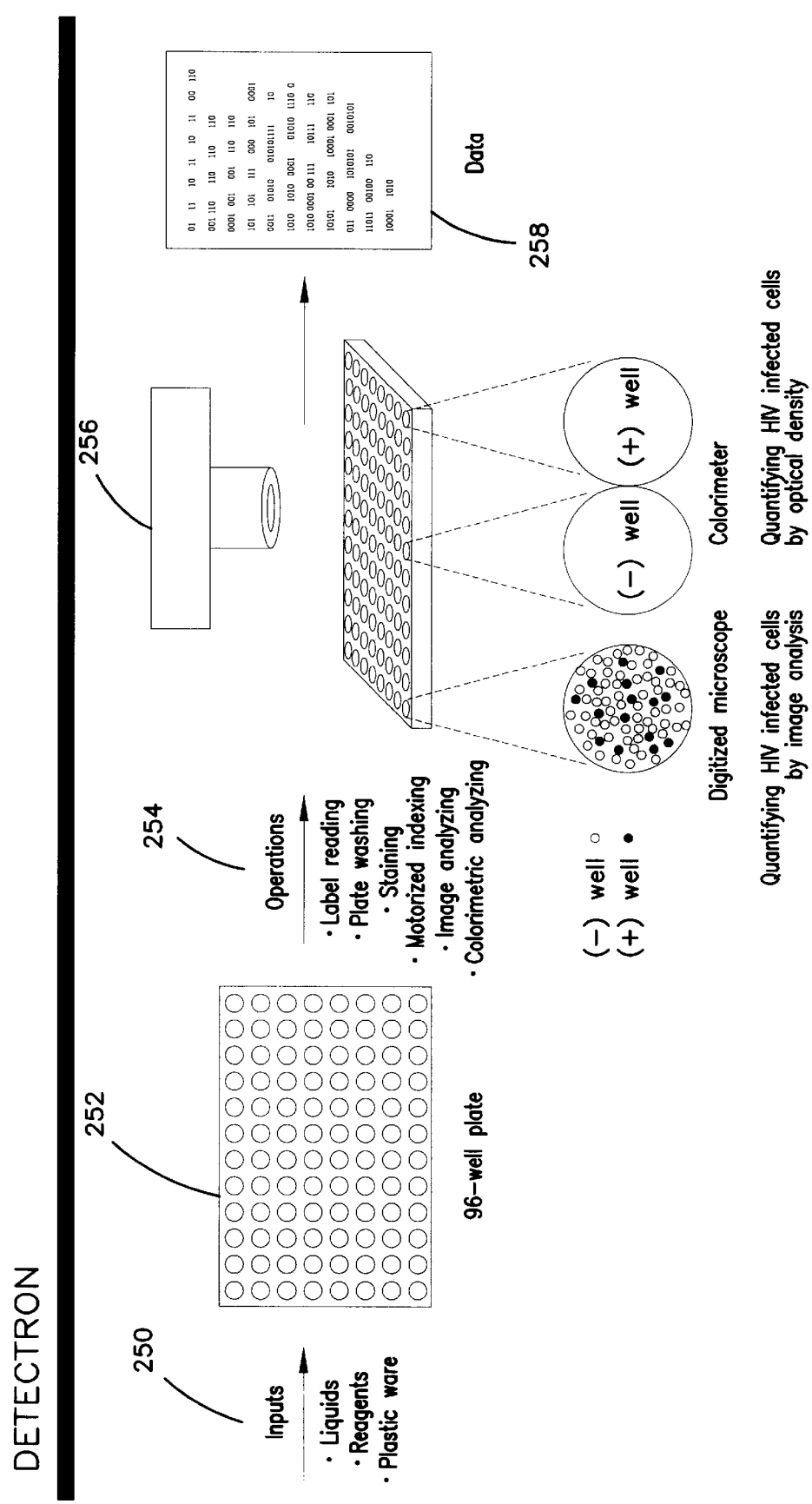

FIG. 9 presents an overview of the process steps for performing detection of HIV-infected target cells. These operations are performed by a group of SLMs and SSMs hereinafter referred to as an detectron 135B. The detectron 135B accepts liquids, reagents, and plastic ware as well as the 96-well plates 250 as inputs. The detectron 135B then performs a number of detectron operations 254 including label reading, plate washing, staining, motorized indexing, and image and colorimetric analysis. To score wells in colorimetry, cell monolayers are lysed with detergents and viral antigens, and the supernatants are measured by HIV enzyme-linked immuno-sorbent assay (ELISA). Readouts from this process include the number of ± wells per 2 ml centrifuge tube, which can be used for calculating the ID-50 and confidence limits by numerical analysis. To score wells by image analysis, cell monolayers are stained with anti-HIV immunoglobins and HIV-expressing cells are counted by imaging system. Readouts from this process include the number of HIV-expressing cells per 2 ml centrifuge tube, which are used for calculating the viral titer and confidence limits by numerical analysis.

Statistical properties of the quantitative HIV infectivity assay depends on the total number of wells plated per 2 ml centrifuge tube (replicates). In general, results from counting each positive cell (image analysis) are far more precise than ID-50 methods (colorimetry). Methods based on the VAC-MAN computer program can be used for all ID-50 analyses. VACMAN applies Bayesian methods to the analysis of raw data and was developed by Dr. John L. Spouge at the National Library of Medicine.

Figure 10:
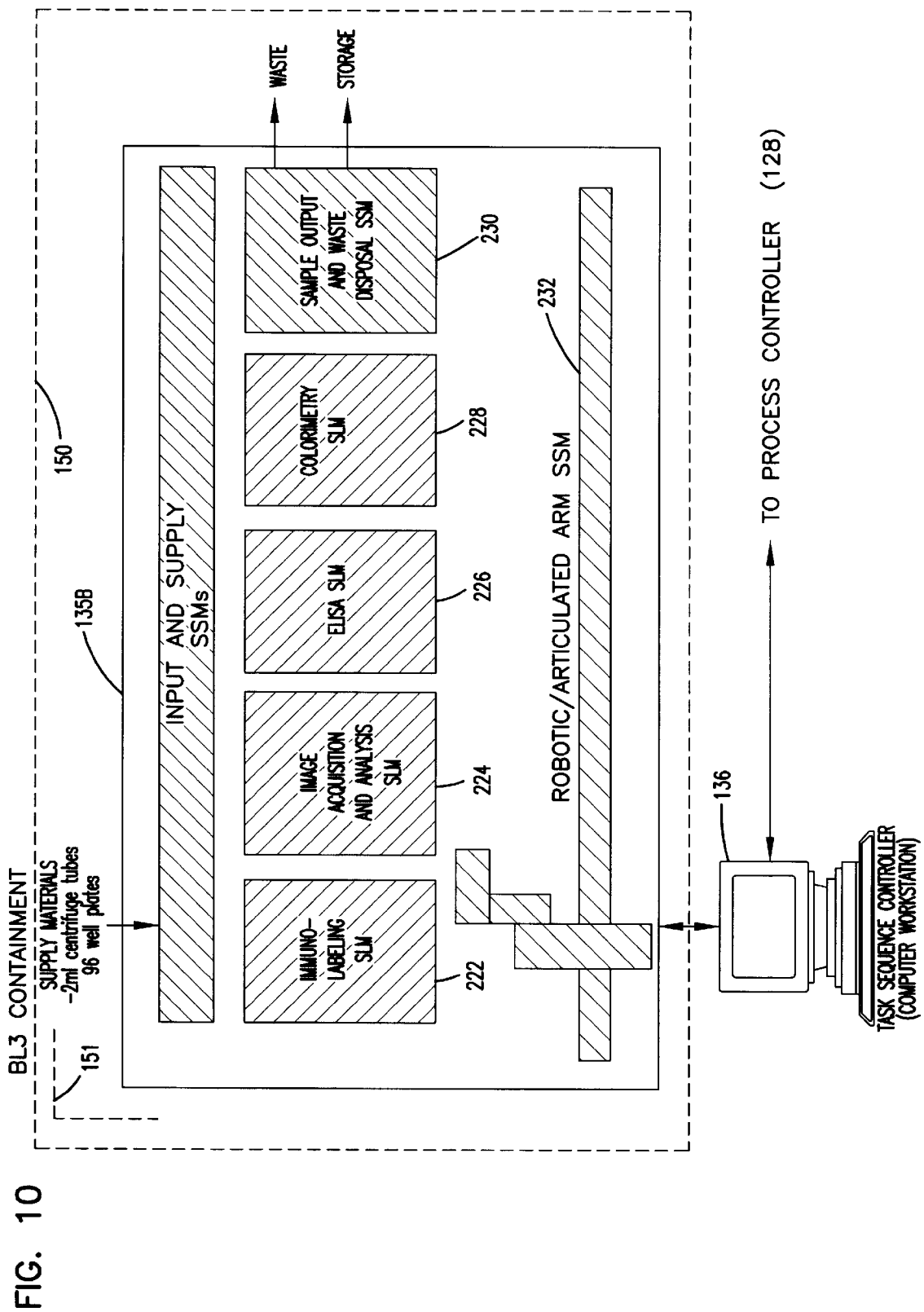

FIG. 10 further illustrates the detectron 135B operations, and how the SLMs 134 and SSMs 132 are employed to implement these operations. Like the infectron 135A, the detectron 135B is securely contained within a BL3 containment facility and biological cabinets when required. The detectron 135B is communicatively coupled to task sequence controller 136, which interfaces with the process controller 128. In the illustrated embodiment, both the infectron 135A and the detectron 135B use the same task sequence controller. However, separate task sequence controllers 136 for the infectron 135A and the detectron 135B can be implemented as well, increasing reliability and autonomy of the infectron 135A and detectron 135B.

The as with the infectron 135A, the detectron 135B comprises one or more input and supply SSMs 220, an immunolabeling SLM 222, an image acquisition and analysis SLM 224, an ELISA SLM 226, a colorimetry SLM 228, a sample output and waste disposal SSM 230, and a inter-module transport SSM 232.

Input and supply SSMs 220 perform functions analogous to hose of the infectron 135A. The input and supply SSMs 220 obtain he 96-well plates, pipette tips, and liquid reagents such as ELISA solutions, fluorescent probes and labeled immunoglobulins. However, in addition, these SSMs also retrieve and uncover the 96-well plates just prior to their use. Intermodule transport SSM 232 passes items between the SLMs and SSMs. In one embodiment, the intermodule transport SSM 232 comprises a robotic/articulated arm such as the ORCA products produced by Sagian Incorporated™. These articulated arms travel along linear tracks, and have acceptable positioning tolerances, degrees of freedom and controller software for high precision manipulations.

The immunolabeling SLM 222 performs all of the steps associated with fixing and staining HIV-infected target cells in the 96-well plates. A modified Beckman Biomek 2000™ or similar device can be employed to perform these SLM functions.

The image acquisition and analysis SLM 224 detects individual HIV-infected cells within cell monolayers, and collects observable data. In one embodiment, the image acquisition and analysis SLM comprises a digital image analysis system and motorized microscope stages capable of handling the 96-well plates.

The ELISA SLM 226 performs all of the solution and handling tasks associated with colorimetric development of infected cell monolayers in 96-well plates.

The Colorimetry SLM 228 performs colorimetry measurements of the treated specimens in the 96-well plates. This device has fast sampling response time, motorized stage, and software for process control.

Sample output and waste disposal SSM 230 disposes of the 96-well plates 212 as well as other waste materials including contaminated 96-well plates, pipette tips and culture media. Waste materials are disposed (i.e. collected in containers containing a bleach solution) at the relevant support modules.

Both the infectron 135A and the detectron 135B are designed for handing a wide range of viral assay conditions, permitting many different types of investigation.

The infectron 135A and detectron 135B incorporate a variety of important features. They are designed for easy use by non-engineering scientists and technicians, promoting greater accessibility for research. They also handle a wide range of viral assay conditions, permitting many types of investigation. They will perform numerous assays in parallel with dynamic scheduling and rescheduling capabilities, simplifying the starting and stopping of experiments. They also use advantage of bar coding technologies for sample tracking and database management, facilitating a high throughput research environment. The process controller 128 also provides high-level tools to remote clients 100 that allow programming of SLM controllers on the fly, enabling one instrument to perform any number of unique experiments, such as the biological assays described above. The infectron 135A and detectron 135B contain standard laboratory modules that are removable and interchangeable, permitting easier maintenance and design improvements. The infectron 135A and detectron 135B also comprise tolerance and error checking capabilities within relevant modules, allowing the operator to test and verify the performance of the automated instrument.

Figure 11:
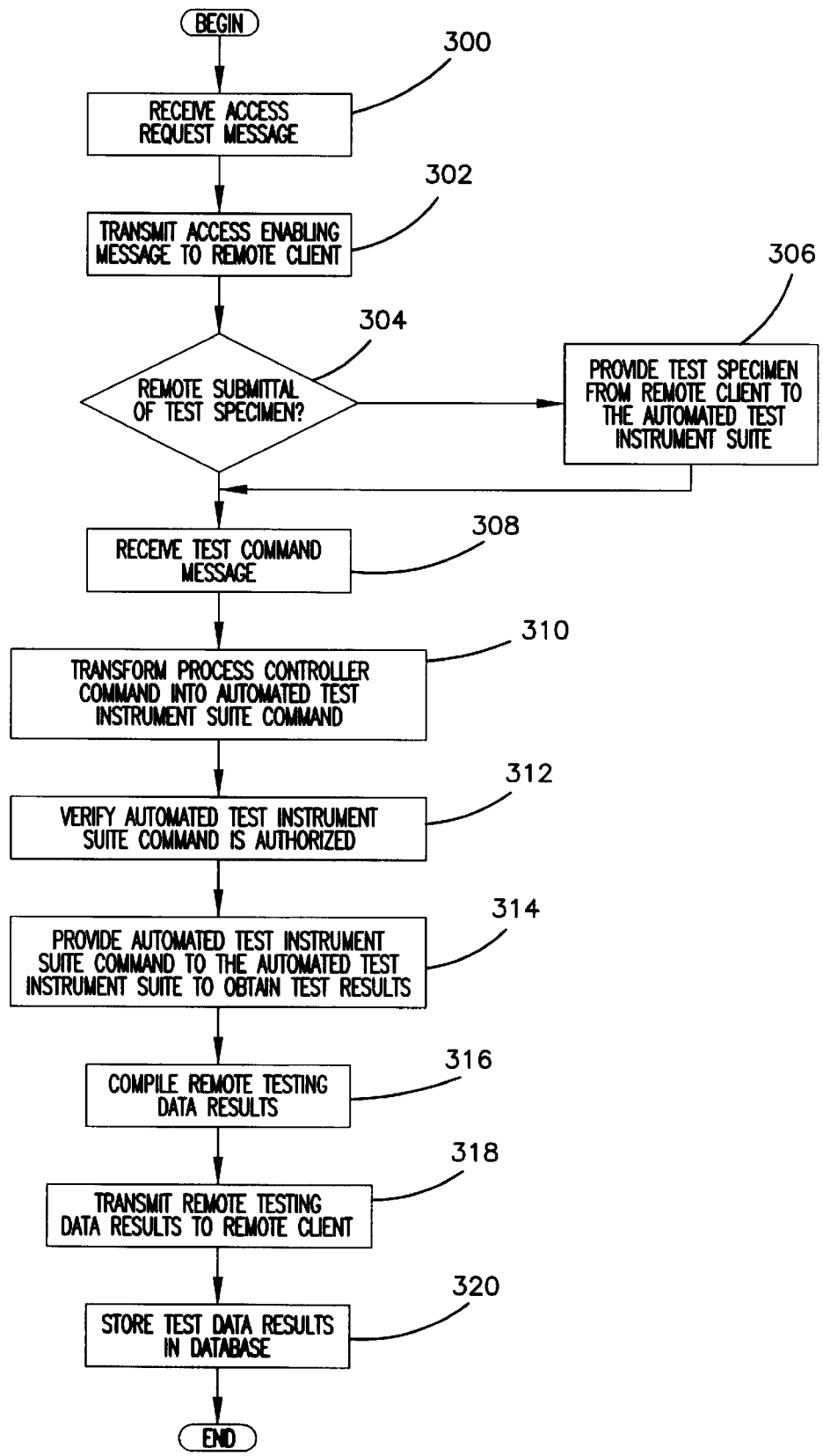

FIG. 11 presents a flow diagram of the operations performed by the present invention. The process begins when the process controller 128 receives an access request message from the remote client 100 via communication link 126. Using information in the access request message and any other available information, the process controller 128 determines if the remote client is authorized to access the automated test instrument suite 130. If so, an access enabling message is transmitted from the process controller 128 to the remote client 100. In one embodiment, the access enabling message comprises a set of computer instructions transmitted over the internet which are thereafter downloaded into the remote client memory 122 for execution by the remote client processor 120. These instructions may be completely enabling, that is, they may allow direct communication between the remote client 100 and the automated test instrument suite 130 with no further need for the process controller 128. Alternatively, the access enabling message may merely share instructions and information between the remote client 100 and the process controller 128, thereby splitting the functionality so that both entities are required to command the test instrument suite 130. In another embodiment, the access enabling message may simply comprise a password or other enabling message which allows the remote client 100 to proceed.

If the remote client 100 desires, a test specimen may be submitted to the automated test instrument suite 130 by commercially available carriers or other means. This activity is depicted in blocks 304 and 306. Of course, the test specimen may be submitted at any time before the test proceeds. Alternatively, the test specimen can be transmitted to the automated test instrument suite first, evaluated using the process control tools 124 described herein, and the data from this activity used to define test procedures.

Next, the process controller 128 receives 308 a test command message defining the test procedures defined by the remote client 100. The test command comprises one or more process controller commands, which allow use of the process control tools 124 and related functions. If necessary, these process controller commands are then further transformed 310 into automated test instrument suite commands, which define the "configurations" or other programmable tasks to be carried out by the SSMs 132 and SLMs 134.

After these commands are verified 312 to assure that they are authorized and will not result in hazardous activity, they are provided 314 to the automated test instrument suite 130 components, including the task sequence controller 136, and thereafter, the SSMs 132 and SLMs 134. The resulting testing data results are then compiled 316 and transmitted 318 to the remote client 100. If the remote client 100 desires, the test data results can be stored 320 in database 138.

Figure 12:
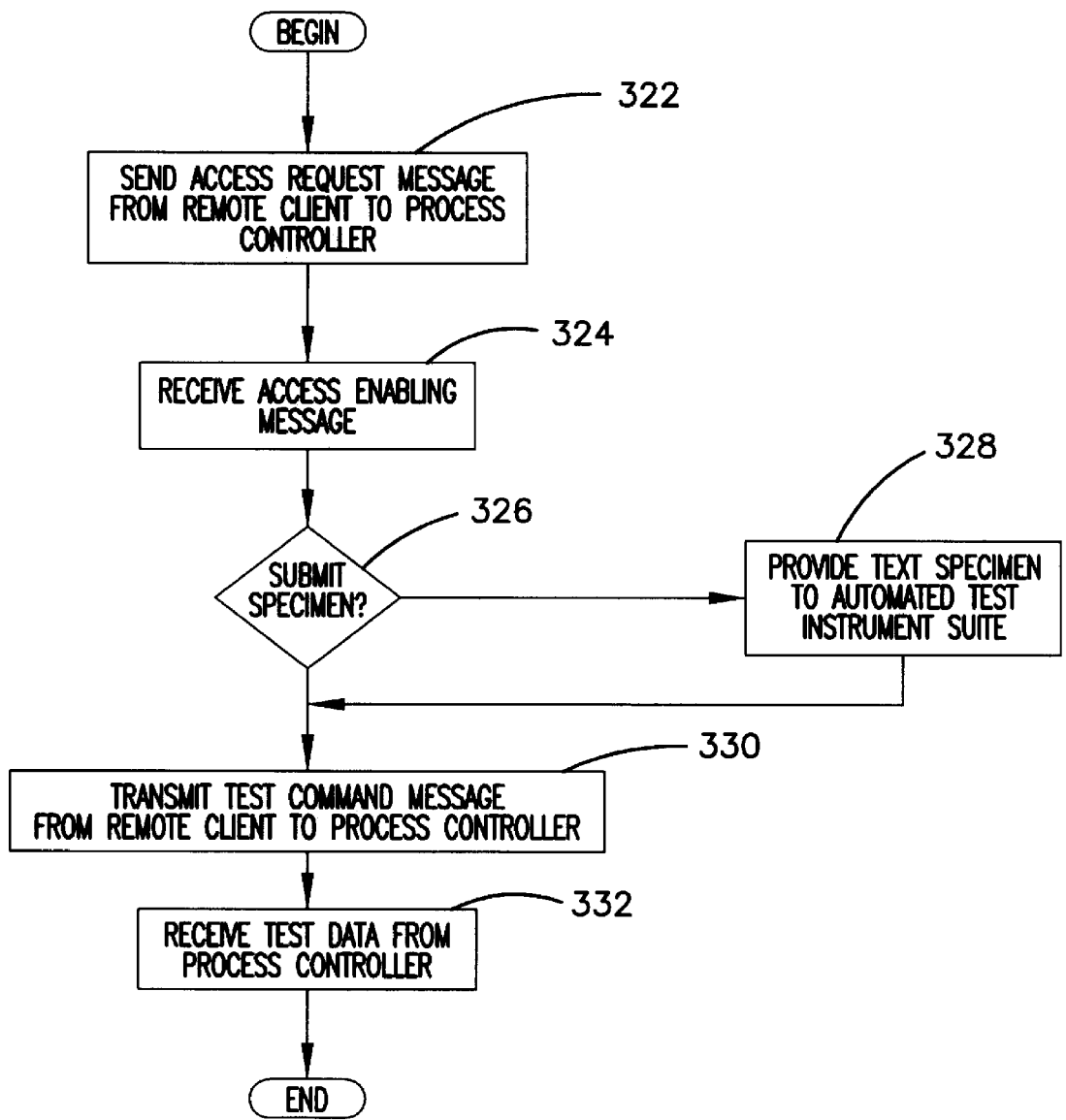

FIG. 12 is a flow chart depicting the method steps employed by the remote client 100 in the present invention. First, the remote client sends 322 an access request message to the process controller 322 via the internet or other communication link 126. Next, the remote client 100 receives 324 an access enabling message from the process controller 128, the contents of which as been described. If the tests involve a test specimen, the remote client 100 can submit the specimen to the automated test instrument suite 130 for testing. This is depicted in blocks 326 and 328. The remote client 100 then transmits 130 a test command message to the process controller 128 which interprets and processes this message to perform the test procedures described therein. After the tests are complete, the remote client 100 receives the test data from the process controller 128.

CONCLUSION

As the above demonstrates, there is a need for providing testing and data dissemination services to a wide variety of globally-distributed remote clients. There is also a need to integrate the capabilities of available automated test equipment to permit a broad range of automated tests to be performed without special-purpose devices. This need is especially critical when applied the study of the physical properties of rapidly mutating infections antigens, such as the HIV virus. The present invention satisfies this need by providing an apparatus and method which provides a wide variety of adaptable testing services to globally-distributed remote clients.

What is claimed is:

1. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions perfomable by the remote client to generate a test command message, the test instrument suite including an operation process control toolset;

receiving a test command message from the remote client in the process controller via the communications link, the test command message comprising a process controller command;

transforming the process controller command into at least one automated test instrument suite command, and wherein the automated test instrument suite command permits for a selection, by the remote client, of different test protocols with the process control toolset;

providing the automated test instrument suite command to the automated test instrument suite to obtain remote testing data results;

compiling the remote testing data results; and transmitting the compiled remote testing data results to the remote client.

2. The method of claim 1, further comprising the step of verifying that the automated test instrument suite commands are authorized.

3. The method of claim 1, wherein an alert message is transmitted from the process controller when the selected remote testing options are not authorized.

4. The method of claim 1, wherein the process control toolset further comprises information describing how to use the automated test instrument suite.

5. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions performable by the remote client to generate a test a command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results;

transmitting the complied remote testing data results to the remote client; and wherein the process control toolset further comprises computer program instructions for performing simulations at the remote client of the automated test instrument suite operations.

6. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions performable by the remote client to generate a test command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results;

transmitting the compiled remote testing data results to the remote client; and wherein the process control toolset further comprises a plurality of standard automated test instrument suite operations.

7. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions performable by the remote client to generate a test command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results;

transmitting the compiled remote testing data results to the remote client; and wherein the automated test instrument suite comprises a database for storing, retrieving, comparing, and analyzing test data and a plurality of interoperable automated test equipment modules.

8. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions performable by the remote client to generate a test command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results;

transmitting the compiled remote testing data results to the remote client; and wherein the process control toolset further comprises computational tools for analyzing the remote testing data results.

9. A method of sharing integrated testing services with at least one autonomous remote client, comprising the steps of:

receiving an access request message from the remote client in a process controller via a communications link, the process controller communicatively coupled to a sharable automated test instrument suite;

transmitting an access enabling message from the process controller to the remote client via the communications link when the remote client is authorized to access the integrated testing services, the access enabling message having a process control toolset including instructions performable by the remote client to generate a test command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results;

transmitting the compiled remote testing data results to the remote client;

wherein:
   the method further comprises the step of providing a test specimen received from the remote client to the automated test instrument suite; and
   the test message comprises automated test suite instructions to perform tests on the test specimen.

10. The method of claim 9, wherein the process control toolset further comprises information describing how to prepare the test specimen for testing by the automated test instrument suite.

11. The method claim 9, further comprising the step of storing the complied remote testing data results in the database.

12. The method of claim 9, wherein
the test command message further comprises test specimen background information; and
the method further comprises the step of storing the specimen information in the database.

13. The method of claim 9, wherein the process control toolset further comprises process controller commands for controlling access to data generated by the remote client.

14. The method of claim 9, wherein the specimen is potentially infected with a retrovirus, and the automated test instrument suite comprises:
means for treating the specimen to manifest an observable result, the observable result being selected from the infectious fraction of the virus, the reproductive number of the virus, the number of copies of an envelope protein or core protein associated with the virus, the number of copies of reverse transcriptase associated with the virus, the rate of spontaneous degradation of the virus, the genetic classification of the virus as determined by sequence hybridization, and the serotype of the virus as determined by reactivity with a panel of immunoglobins; and
means for controlling the means for treating the specimen in order to perform high throughput humoral, infectious testing on the specimen.

15. The method of claim 14, wherein the automated test instrument suite further comprises means for measuring the observable result to generate the remote data testing results in response to the automated test instrument suite command.

16. The apparatus of claim 14, wherein the automated test instrument suite further comprises means for measuring the observable result to generate the remote data testing results in response to the automated test instrument suite command.

17. A method of sharing integrated testing services with at least one autonomous remote client, comprising the steps of:
sending an access request message from the remote client to a process controller via a communications link, the process controller communicatively coupled to a sharable automated test instrument suite;
receiving an access enabling message from the process controller to the remote client via the communications link when the remote client is authorized to access the integrated testing services, the access enabling message having a process control toolset including instructions performable by the remote client to generate a test command message, the test instrument suite including an operation process control toolset;
transmitting the test command message from the remote client in the process controller via the communications link, the test command message comprising a process controller command interpretable into test instrument suite commands for commanding the automated test instrument suite to obtain remote testing data results, the first instrument suite including different test protocols with the process control toolset, the different protocols being selectable by the remote client; and
receiving testing data results from the process controller.

18. The method of claim 17 wherein the process control toolset further comprises information describing how to use the automated test instrument suite.

19. A method of sharing integrated testing services with at least one autonomous remote client, comprising the steps of:

sending an access request message from the remote client to a process controller via a communications link, the process controller communicatively coupled to a sharable automated test instrument suite;
receiving an access enabling message from the process controller to the remote client via the communications link when the remote client is authorized to access the integrated testing services, the access enabling message having a process control toolset including instructions performable by the remote client to generate a test command message;
transmitting the test command message from the remote client in the process controller via the communications link, the test command message comprising a process controller command interpretable into test instrument suite commands for commanding the automated test instrument suite to obtain remote testing data results;
receiving testing data results from the process controller; and
wherein the process control toolset further comprises computer program instructions for performing simulations at the remote client of the automated test instrument suite operations.

20. A method of sharing integrated testing services with at least one autonomous remote client, comprising the steps of:
sending an access request message from the remote client to a process controller via a communications link, the process controller communicatively coupled to a sharable automated test instrument suite;
receiving an access enabling message from the process controller to the remote client via the communications link when the remote client is authorized to access the integrated testing services, the access enabling message having a process control toolset including instructions performable by the remote client to generate a test command message;
transmitting the test command message from the remote client in the process controller via the communications link, the test command message comprising a process controller command interpretable into test instrument suite commands for commanding the automated test instrument suite to obtain remote testing data results;
receiving testing data results from the process controller; and
wherein the process control toolset further comprises a plurality of standard automated test instrument suite operations.

21. A method of sharing integrated testing services with at least one autonomous remote client, comprising the steps of:
sending an access request message from the remote client to a process controller via a communications link, the process controller communicatively coupled to a sharable automated test instrument suite;
receiving an access enabling message from the process controller to the remote client via the communications link when the remote client is authorized to access the integrated testing services, the access enabling message having a process control toolset including instructions performable by the remote client to generate a test command message;
transmitting the test command message from the remote client in the process controller via the communications link, the test command message comprising a process controller command interpretable into test instrument suite commands for commanding the automated test instrument suite to obtain remote testing data results;

receiving testing data results from the process controller; and wherein the automated test instrument suite comprises a database for storing, retrieving comparing, and analyzing test data and a plurality of interoperable automated test equipment modules.

22. A method of sharing integrated testing services with at least one autonomous remote client, comprising the steps of:

sending an access request message from the remote client to a process controller via a communications link, the process controller communicatively coupled to a sharable automated test instrument suite;

receiving an access enabling message from the process controller to the remote client via the communications link when the remote client is authorized to access the integrated testing services, the access enabling message having a process control toolset including instructions performable by the remote client to generate a test command message;

transmitting the test command message from the remote client in the process controller via the communications link, the test command message comprising a process controller command interpretable into test instrument suite commands for commanding the automated test instrument suite to obtain remote testing data results;

receiving testing data results from the process controller; and wherein the process control toolset further comprises computational tools for analyzing the remote testing data results.

23. A method of sharing integrated testing services with at least one autonomous remote client, comprising the steps of:

sending an access request message from the remote client to a process controller via a communications link, the process controller communicatively coupled to a sharable automated test instrument suite;

receiving an access enabling message from the process controller to the remote client via the communications link when the remote client is authorized to access the integrated testing services, the access enabling message having a process control toolset including instructions performable by the remote client to generate a test command message;

transmitting the test command message from the remote client in the process controller via the communications link, the test command message comprising a process controller command interpretable into test instrument suite commands for commanding the automated test instrument suite to obtain remote testing data results;

receiving testing data results from the process controller; and further comprising the step of providing a test specimen to the automated test instrument suite.

24. An apparatus for sharing integrated testing services with at least one autonomous remote client, comprising:

means for receiving an access request message from the remote client in a process controller via a communications link, the process controller communicatively coupled to a sharable automated test instrument suite, the test instrument suite including a plurality of different test operation;

means for transmitting an access enabling message from the process controller to the remote client via the communications link when the remote client is authorized to access the integrated testing services, the access enabling message having a process control toolset including instructions performable by the remote client to generate a test command message, the test instrument suite including an operation process control toolset;

means for receiving a test command message from the remote client in the process controller via the communications link, the test command message comprising a process controller command;

means for transforming the process controller command into at least one automated test instrument suite command, and wherein the automated test instrument suite command permits for a selection, by the remote client, of different test protocols with the process control toolset;

means for providing the automated test instrument suite command to the automated test instrument suite to obtain remote testing data results;

means for compiling the remote testing data results; and means for transmitting the compiled remote testing data results to the remote client.

25. The apparatus of claim 24, further comprising means for verifying that the automated test instrument suite commands are authorized.

26. The apparatus of claim 24, wherein an alert message is transmitted from the process controller when the selected remote testing options are not authorized.

27. The apparatus of claim 24, wherein the process control toolset further comprises information describing how to use the automated test instrument suite.

28. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the process control toolset further comprises computer program instructions for performing simulations at the remote client of the automated test instrument suite operations.

29. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the process control toolset further comprises a plurality of standard automated test instrument suite operations.

30. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the complied remote testing data results to the remote client; and wherein the automated test instrument suite comprises a database for storing, retrieving, comparing, and analyzing test data and a plurality of interoperable automated test equipment modules.

31. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the process control toolset further comprises computational tools for analyzing the remote testing data results.

32. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the process control toolset further comprises information describing how to prepare the test specimen for testing by the automated test instrument suite.

33. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the complied remote testing data results to the remote client; and further comprising means for storing the compiled remote testing data results in the database.

34. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the test command message further comprises test specimen background information, and the apparatus further comprises means for storing the specimen information in the database.

35. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results;

means for transmitting the compiled remote testing data results to the remote client; and wherein the process control toolset further comprises process controller commands for controlling access to data generated by the remote client.

36. An apparatus for sharing integrated testing services with at least one autonomous remote client, comprising:

means for receiving an access request message from the remote client in a process controller via a communications link, the process controller communicatively coupled to a sharable automated test instrument suite;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automates test instrument suite command;

means for providing the automated test instrument suite command to the automated test instrument suite to obtain remote testing data results;

means for compiling the remote testing data results;

means for transmitting the compiled remote testing data results to the remote client; and wherein the specimen is potentially infected with a retrovirus, and the automated test instrument suite comprises:

means for treating the specimen to manifest an observable result, the observable result being selected from the infectious fraction of the virus, the reproductive number of the virus, the number of copies of an envelope protein or core protein associated with the virus, the number of copies of reverse transcriptase associated with the virus, the rate of spontaneous degradation of the virus, the genetic classification of the virus as determined by sequence hybridization, and the serotype of the virus as determined by reactivity with a panel of immunoglobins; and means for controlling the means for treating the specimen in order to perform high throughput humoral, infectious testing on the specimen.

37. A method of sharing integrated testing services with at least one autonomous remote client, comprising the steps of:

receiving an access request message from the remote client in a process controller via a communications link, the process controller communicatively coupled to a sharable automated test instrument suite, and the remote client being at a sit removed from the instrument, such that the communication link includes an Internet link;

transmitting an access enabling message from the process controller to the remote client via the communications link when the remote client is authorized to access the integrated testing services, the access enabling message having a process control toolset including instructions performable by the remote client to generate a test command message;

receiving a test command message from the remote client in the process controller via the communications link, the test command message comprising a process controller command;

transforming the process controller command into at least one automated test instrument suite command;

providing the automated test instrument suite command to the automated test instrument suite to obtain remote testing data results;

compiling the remote testing data results; and transmitting the compiled remote testing data results to the remote client.

38. A method of sharing integrated testing services with at least one autonomous remote client, comprising the steps of:

sending an access request message from the remote client to a process controller via a communications link, the process controller communicatively coupled to a sharable automated test instrument suite, and the remote client being at a site removed from the instrument, such that the communication link includes an Internet link;

receiving an access enabling message from the process controller to the remote client via the communications link when the remote client is authorized to access the integrated testing services, the access enabling message having a process control toolset including instructions performable by the remote client to generate a test command message;

transmitting the test command message from the remote client in the process controller via the communications link, the test command message comprising a process controller command interpretable into test instrument suite commands for commanding the automated test instrument suite to obtain remote testing data results; and receiving testing data results from the process controller.

39. An apparatus for sharing integrated testing services with at least one autonomous remote client, comprising:

means for receiving an access request message from the remote client in a process controller via a communications link, the process controller communicatively coupled to a sharable automated test instrument suite, and the remote client being at a site removed from the instrument, such that the communication link includes an Internet link;

means for transmitting an access enabling message from the process controller to the remote client via the communications link when the remote client is authorized to access the integrated testing services, the access enabling message having a process control toolset including instructions performable by the remote client to generate a test command message;

means for receiving a test command message from the remote client in the process controller via the communications link, the test command message comprising a process controller command;

means for transforming the process controller command into at least one automated test instrument suite command;

means for providing the automated test instrument suite command to the automated test instrument suite to obtain remote testing data results;

means for compiling the remote testing data results; and means for transmitting the compiled remote testing data results to the remote client.

* * * * *